United States Patent [19]

Trijzelaar et al.

[11] Patent Number: 4,472,403
[45] Date of Patent: Sep. 18, 1984

[54] QUINOLINE DERIVATIVES AND PHARMACEUTICAL COMPOSITIONS AND METHODS FOR TREATING CARDIOVASCULAR DISEASE WITH SUCH COMPOUNDS

[75] Inventors: Hans B. Trijzelaar, Zeist; Ronus de Bode, Bilthoven; Hendricus B. A. Welle, Maarssen, all of Netherlands

[73] Assignee: A.C.F. Chemiefarma N.V., Netherlands

[21] Appl. No.: 201,577

[22] Filed: Oct. 28, 1980

[30] Foreign Application Priority Data

Nov. 1, 1979 [NL] Netherlands ................... 7908031

[51] Int. Cl.³ .................... A61K 31/47; C07D 401/06
[52] U.S. Cl. ................................. 424/258; 546/168; 546/174; 546/176; 546/177
[58] Field of Search ............... 546/176, 177, 167, 168, 546/174; 424/258

[56] References Cited

U.S. PATENT DOCUMENTS 3,953,453  4/1976  Grethe et al. ................... 546/134
4,237,139  12/1980  Champseix et al. ............ 424/258
4,238,612  12/1980  Barieux et al. .................. 546/153
4,299,835  11/1981  Champseix et al. ............ 424/258

FOREIGN PATENT DOCUMENTS 0030044   6/1981  European Pat. Off. ........... 424/258
0031753   7/1981  European Pat. Off. ........... 424/258
2315148  10/1973  Fed. Rep. of Germany .
2206944   6/1974  France ............................ 546/177
7908030   6/1981  Netherlands ..................... 424/258

OTHER PUBLICATIONS

Lyle et al., Tetrahedron, vol. 23, No. 8, pp. 3253–3263, (1967).
Gutzwiller et al., J. Am. Chem. Soc., vol. 100, No. 2, pp. 576–581, (01/18/78).
Heidelberger, et al., J. AM. Chem. Soc., vol. 44, pp. 1098–1107, (1922).
Dawes, British J. Pharmacol., 1, pp. 90–111, (1946).

Primary Examiner—Donald G. Daus
Assistant Examiner—Diana G. Rivers
Attorney, Agent, or Firm—Jacobs & Jacobs

[57] ABSTRACT

The invention is concerned with novel quinicine and cinchonicine derivatives having cardiovascular activities of the formula or a salt thereof,

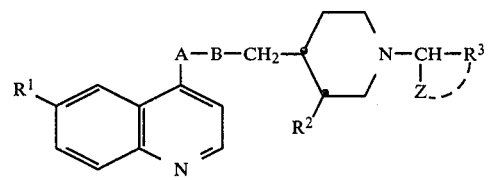

in which A—B is —$CH_2$—$CH_2$, —CHOH—$CH_2$—, —$CH_2$—CHOH—, —C(O)—$CH_2$—, —$CH_2$—C(O)—, —C($NOR^4$)—$CH_2$— or —$CH_2$—C($NOR^4$)—; $R^1$ is hydrogen, hydroxy or lower alkoxy; $R^2$ is ethyl or vinyl; $R^3$ is $C_{2-8}$ alkyl, $C_{1-8}$ hydroxyalkyl, lower alkoxyalkyl or lower alkanoyloxyalkyl, $C_{3-6}$ cycloalkyl, hydroxycycloalkyl, lower alkoxycycloalkyl or lower alkanoyloxycycloalkyl, cycloalkyl lower alkyl, hydroxy-, lower alkoxy- or lower alkanoyloxycycloalkyl lower alkyl; cyano, cyano lower alkyl, lower alkenyl, lower alkynyl, tetrahydrofuryl, mono- or di-lower alkylamino lower alkyl, mono- or di-lower alkylamino lower hydroxy alkyl; optionally substituted phenyl, phenyl lower alkyl or phenyl hydroxy lower alkyl, optionally substituted diphenyl lower alkyl, optionally substituted phenyl lower alkenyl, optionally substituted benzoyl or benzoyl lower alkyl, optionally substituted heteroaryl or heteroaryl lower alkyl, or optionally substituted heteroaroyl or heteroaroyl lower alkyl; $R^4$ is lower alkyl, and Z is hydrogen, lower alkyl or optionally substituted phenyl, or Z and $R^3$ together with the carbon atom to which they are attached form a $C_{3-6}$ cycloalkyl group, whereby the substituents at the 3- and 4-position of the piperidine ring are in the cis-position, excluding N-[$C_{2-6}$ alkyl, $C_{2-6}$ hydroxyalkyl, NN-di-lower alkylamino lower alkyl, optionally substituted $C_{7-11}$ aralkyl] substituted derivatives of quinicine and cinchonicine.

The compounds of the formula may be in the form of their optically active enantiomers and/or their therapeutically acceptable salts.

Methods for the preparation of the compounds of the formula are also disclosed and form part of the invention.

22 Claims, No Drawings

QUINOLINE DERIVATIVES AND PHARMACEUTICAL COMPOSITIONS AND METHODS FOR TREATING CARDIOVASCULAR DISEASE WITH SUCH COMPOUNDS

The invention relates to novel quinoline derivatives.

In French patent publication 2,177,511 and the corresponding German patent application 2,315,148 quinoline derivatives are described with formula 2

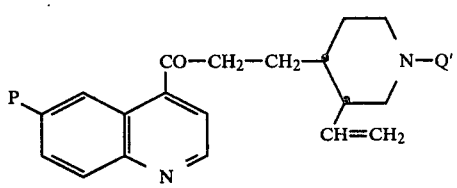

in which P is hydrogen or methoxy and Q' is $C_{2-6}$ alkyl, optionally substituted by alkoxycarbonyl, hydroxy or —NR'R" in which R' and R" each represent $C_{1-4}$ alkyl or together with the nitrogen to which they are attached form a 5–7 membered heterocyclic ring, which may have oxygen or nitrogen as a second hetero atom, the second nitrogen atom being optionally substituted, R" may also represent $C_{7-11}$ aralkyl, optionally substituted by halogen, $C_{1-6}$ alkyl or $C_{1-6}$ alkoxy, which compounds have anti-spasmodic and vasodilative activity.

From Ann. Pharm. Fr. 24, 39 (1966) the pharmacodynamic properties of quinicine (formula 3), also named viquidil, are known, in particular in the field of CNS, hypotensive, vasodilative and anti-spasmodic activities.

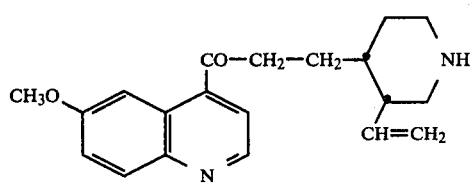

In British Pat. 1,294,538 the use of viquidil in the treatment of cerebral vessel injury, cerebrovascular insufficiency and memory deficiency in humans is described.

In Dutch patent application 77,06614 quinoline derivatives are described with formula 4.

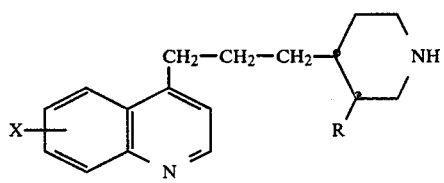

in which R is hydrogen, $C_{1-4}$ alkyl or $C_{2-4}$ alkenyl and X is hydrogen, halogen, $C_{1-4}$ alkyl, alkoxy or alkylthio, trifluoromethyl, nitro, hydroxy, an amino group optionally substituted by one or two $C_{1-4}$ alkyl groups, or $C_{1-4}$ acyl or alkylsulphonyl group, which compounds have a serotonin uptake inhibiting effect and anti-arrhythmic activity.

It has now been found, that qunioline derivatives with a substituent at the 4-position containing a N-substituted piperidyl group, possess unexpected pharmacological properties, namely desirable effects on the cardiovascular system, such as anti-hypertensive, anti-thrombotic, vasodilative and anti-arrhythmic activity. The compounds are particularly useful for use in medicines having anti-hypertensive and anti-arrhythmic activity.

Thus, the invention provides compounds of formula 1,

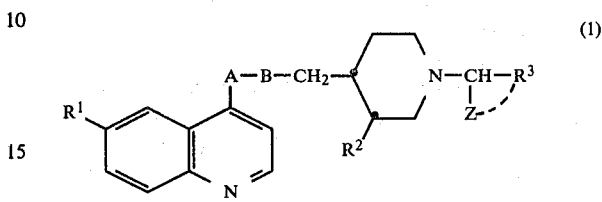

in which

A—B is —$CH_2$—$CH_2$—, —CHOH—$CH_2$—, —$CH_2$—CHOH—, —C(O)—$CH_2$—, —$CH_2$—C(O)—, —C(NOR$^4$)—$CH_2$— or —$CH_2$—C(NOR$^4$)—, $R^1$ is hydrogen, hydroxy or lower alkoxy, $R^2$ is ethyl or vinyl, $R^3$ is $C_{2-8}$ alkyl, $C_{1-8}$ hydroxyalkyl, lower alkoxyalkyl or lower alkanoyloxyalkyl, $C_{3-6}$ cycloalkyl, hydroxycycloaklyl, lower alkoxycycloalkyl or lower alkanoyloxycycloalkyl, cycloaklyl lower alkyl, hydroxy-, lower alkoxy- or lower alkanoyloxycycloalkyl lower alkyl; cyano, cyano lower alkyl, lower alkenyl, lower alkynyl, tetrahydrofuryl, mono- or di-lower alkylamino lower alkyl, mono- or di-lower alkylamino lower hydroxy alkyl; optionally substituted phenyl, phenyl lower alkyl or phenyl hydroxy lower alkyl, optionally substituted diphenyl lower alkyl, optionally substituted phenyl lower alkenyl, optionally substituted benzoyl or benzoyl lower alkyl, optionally substituted heteroaryl or heteroaryl lower alkyl, or optionally substituted heteroaroyl or heteroaroyl lower alkyl, $R^4$ is lower alkyl, and Z is hydrogen, lower alkyl or optionally substituted phenyl, or Z and $R^3$ together with the carbon atom to which they are attached form a $C_{3-6}$ cycloalkyl group, whereby the substituents at the 3- and 4-position of the piperidine ring are in the cis-position, excluding N-[$C_{2-6}$ alkyl, $C_{2-6}$ hydroxyalkyl, NN-di-lower alkylamino lower alkyl, optionally substituted $C_{7-11}$ aralkyl] substituted derivatives of quinicine and cinchonicine.

As is usual, the carbon chains of the different groups may be straight or branched.

The term "lower" is here used to mean a group with up to six carbon atoms.

The term "optionally substituted" with respect to phenyl includes a phenyl group, which may be optionally substituted by one, two or three groups selected from lower alkyl, lower alkoxy, halogen or hydroxy (no more than two hydroxy groups).

The term "optionally substituted" with respect to heteroaryl is here used to mean a heteroaryl group, which may be substituted by one, two or three groups selected from lower alkyl, lower alkoxy or halogen.

Aptly, A—B is —$CH_2$—$CH_2$—. Another suitable meaning of A—B is —CHOH—$CH_2$—. Also suitable is the meaning of A—B being —$CH_2$—CHOH—. Suitably, A—B is —C(0)—$CH_2$—. Also suitably, A—B is —$CH_2$—C(O)—. The meaning of A—B being —C(NOR$^4$)—$CH_2$ is also apt, as well as A—B being —$CH_2$—C(NOR$^4$)—, $R^4$ being preferably methyl. It has been found, that the compounds in which A—B is —CHOH—CH$_2$— are preferred compounds in relation to their therapeutic properties.

Where R$^1$ is alkoxy, it is preferably methoxy. R$^1$ is preferably hydrogen or methoxy. Favourably, R$^1$ is hydrogen. Also favourably, R$^1$ is methoxy.

R$^3$ as alkyl is preferably ethyl. Other suitable alkyl groups include n-butyl, iso-butyl, n-pentyl, iso-pentyl, n-hexyl, n-heptyl or n-octyl.

R$^3$ as cycloalkyl is e.g. cyclopropyl or cyclobutyl.

Suitable values for R$^3$ as hydroxyalkyl, hydroxycycloalkyl or hydroxycycloalkyl lower alkyl include substituents with the formula —(CH$_2$)$_n$C(OH)R$^{4'}$R$^5$, in which n is 0, 1 or 2, R$^{4'}$ is hydrogen or C$_{1-3}$ alkyl and R$^5$ is hydrogen or C$_{1-3}$ alkyl or R$^{4'}$ and R$^5$ together with the carbon atom to which they are attached form a C$_{3-6}$ carbocyclic ring. The meaning of 1-hydroxy-1-methylethyl is particularly suitable.

Favourable values for R$^3$ as alkoxyalkyl, alkoxycycloalkyl or alkoxycycloalkylalkyl include substituents with the formula —(CH$_2$)$_n$—C(OR$^6$)R$^{4'}$R$^5$ in which R$^{4'}$ and R$^5$ are as defined hereinbefore and R$^6$ is C$_{1-3}$ alkyl and n is 0, 1, 2, 3 or 4.

Suitable values for R$^3$ as alkanoyloxyalkyl, alkanoyloxycycloalkyl or alkanoyloxycycloalkylalkyl include substituents with the formula —(CH$_2$)$_n$-C(OCOR$^7$)R$^{4'}$R$^5$, in which n, R$^{4'}$ and R$^5$ are as defined above and R$^7$ is hydrogen or C$_{1-3}$ alkyl.

Where R$^3$ is lower alkynyl, it is preferably ethynyl.

Where R$^3$ is lower alkenyl, it is preferably ethenyl.

Suitable values for R$^3$ as mono- or di-lower alkylamino lower alkyl and hydroxyalkyl include substituents with the formula —(CH$_2$)$_n$NR$^8$R$^9$, in which n is 1 or 2, R$^8$ is hydrogen or C$_{1-3}$ alkyl and R$^9$ is C$_{1-3}$ alkyl.

Suitable values for R$^3$ as optionally substituted phenyl, phenyl lower alkyl or phenylhydroxy lower alkyl include phenyl, benzyl, α-hydroxy-benzyl or benzyl, optionally substituted by 1, 2 or 3 methoxy groups.

Where R$^3$ is optionally substituted diphenyl lower alkyl, it is preferably 3-(4,4'-difluorodiphenyl)propyl.

A favourable value for R$^3$ as optionally substituted phenyl lower alkenyl includes cinnamyl.

Suitable values for R$^3$ as optionally substituted benzoyl or benzoyl lower alkyl include benzoyl, fluorobenzoylmethyl, benzoylmethyl, 2-benzoylethyl, 2-(methylbenzoyl)ethyl, 2-(methoxybenzoyl)ethyl, 2-(chlorobenzoyl)ethyl, 2-(fluorobenzoyl)ethyl and aminobenzoyl. Particularly suitable are the meanings of 2-(4-fluorobenzoyl)ethyl, 2-(4-methoxylbenzoyl)ethyl and 2-(4-methoxybenzoyl)ethyl and 2-benzoylethyl.

Where R$^3$ is heteroaroyl or heteroaroyl lower alkyl, it is aptly monocyclic heteroaromatic ring members containing one or two heteroatoms, of which oxygen, nitrogen or sulfur are preferred, optionally substituted by a lower alkyl group. Favourable values include thienyl and furyl.

Suitable values for Z include hydrogen, methyl, ethyl, n-propyl, isopropyl and phenyl. Preferably, Z is hydrogen.

A particular group of compounds of formula 1 are those of formula 1a

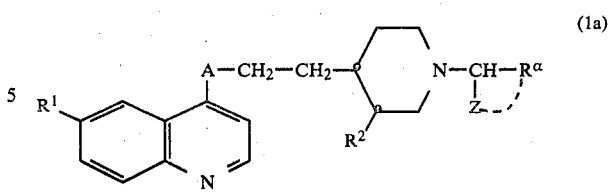

in which
A is —CH$_2$—, —CHOH— or —CO—,
R$^1$ is hydrogen, hydroxy or lower alkoxy,
R$^2$ is ethyl or vinyl,
R$^\alpha$ is C$_{2-8}$ alkyl, C$_{1-8}$ hydroxyalkyl, lower alkoxyalkyl or lower alkanoyloxyalkyl, C$_{3-6}$ cycloalkyl, hydroxycycloalkyl, lower alkoxycycloalkyl or lower alkanoyloxycycloalkyl, cycloalkyl lower alkyl, hydroxy-, lower alkoxy- or lower alkanoyloxycycloalkyl lower alkyl; cyano, cyano lower alkyl, lower alkenyl, lower alkynyl, tetrahydrofuryl, mono- or di-lower alkylamino lower alkyl; mono- or di-lower alkylamino lower hydroxy alkyl; optionally substituted phenyl, phenyl lower alkyl or phenyl hydroxy lower alkyl, optionally substituted diphenyl lower alkyl, optionally substituted phenyl lower alkenyl, optionally substituted benzoyl or benzoyl lower alkyl, optionally substituted heteroaryl or heteroaryl lower alkyl, or optionally substituted heteroaroyl or heteroaroyl lower alkyl, and
Z is hydrogen, lower alkyl or optionally substituted phenyl, or Z and R$^\alpha$ together with the carbon atom to which they are attached form a C$_{3-6}$ cycloalkyl group, excluding the quinicine and cinchonicine derivates as in formula 1.

Another group of particular compounds of formula 1 are those of formula 1b,

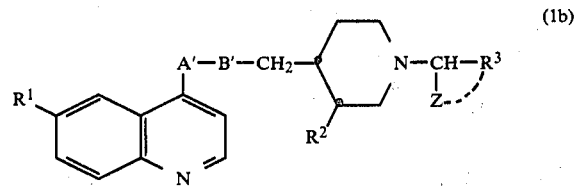

in which R$^1$, R$^2$, R$^3$, R$^4$ and Z are as defined above and A'—B' is —CH$_2$—CH$_2$—, —CHOH—CH$_2$—, —CH$_2$—CHOH—, —CH$_2$—C(O)—, C(NOR$^4$)—CH$_2$— or —CH$_2$—C(NOR$^4$)—.

A further group of particular compounds of formula 1 are those of formula 1c,

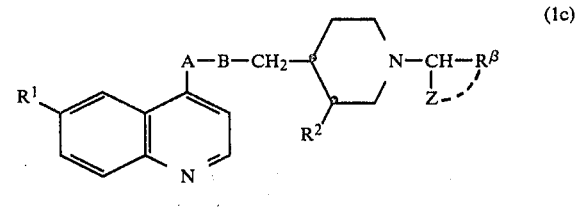

in which
A—B, R$^1$, R$^2$ and Z are as defined above and
R$^\beta$ is C$_{1-8}$ lower alkoxyalkyl or lower alkanoyloxyalkyl, C$_{3-6}$ cycloalkyl, hydroxycycloalkyl, lower alkoxycycloalkyl or lower alkanoyloxycycloalkyl, cycloalkyl lower alkyl, hydroxy-, lower alkoxy- or lower alkanoyloxycyloalkyl lower alkyl; cyano, cyano lower alkyl, lower alkenyl, lower alkynyl, tetrahydrofuryl, mono- or di-lower alkylamino lower hydroxyalkyl; optionally substituted phenylhydroxy lower alkyl, optionally substituted diphenyl lower alkyl, optionally substituted phenyl lower alkenyl, optionally substituted benzoyl or benzoyl lower alkyl, optionally substituted heteroaryl or heteroaryl lower alkyl, or optionally substituted heteroaroyl or heteroaroyl lower alkyl, or Z and R$^\beta$ together with the carbon atom to which they are attached form a C$_{3-6}$ cycloalkyl group.

Preferably, Z is hydrogen.

A particular group of compounds of formula 1 are those of formula 1d

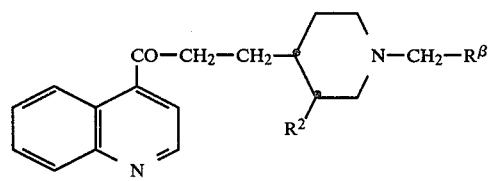

in which R$^2$ and R$^\beta$ are as defined above. In formula 1d we prefer to use R$^2$ as ethyl. Preferably R$^\beta$ is 2-benzoylethyl, 2-(4-fluorobenzoyl)ethyl, 1-hydroxy-1-methyl-ethyl or 3-methoxypropyl.

Another group of preferred compounds of formula 1 are those of formula 1e

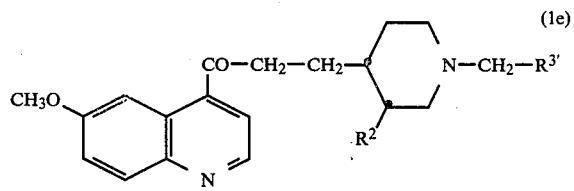

in which R$^2$ is as defined above, R$^{3'}$ is ethyl, n-butyl, isobutyl, n-pentyl, iso-pentyl, lower alkoxy lower alkyl, C$_{3-6}$ cycloalkyl lower alkyl, lower alkenyl, optionally substituted phenyl lower alkyl or optionally substituted benzoyl or benzoyl lower alkyl. R$^2$ is preferably vinyl. Especially preferred are the compounds of formula 1e in which R$^2$ is vinyl and R$^3$ is 2-benzoylethyl, 2-(4-fluorobenzoyl)ethyl or 1-hydroxy-1-methyl-ethyl.

A further group of preferred compounds of formula 1 are those of formula 1f

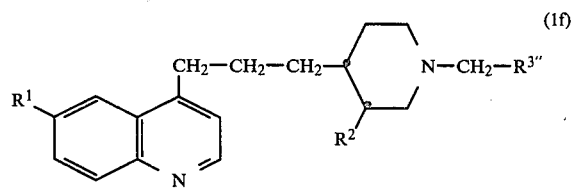

in which R$^1$ and R$^2$ are as defined hereinbefore and R$^{3''}$ is ethyl, n-butyl, iso-butyl, n-pentyl, iso-pentyl, cyclobutyl, lower alkenyl, optionally substituted phenyl lower alkyl or optionally substituted benzoyl or benzoyl lower alkyl. Especially apt are the compounds in which R$^1$ is methoxy, R$^2$ is vinyl and R$^{3''}$ is cyclobutyl, 2-benzoylethyl or 2-(4-fluorobenzoyl)ethyl. Particularly preferred is the compound in which R$^1$ is hydrogen, R$^2$ is ethyl and R$^3$ is 2-benzoylethyl.

A particular group of compounds of formula 1 are those of formula 1g

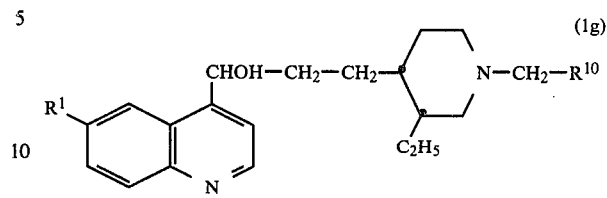

in which R$^1$ is as defined above and R$^{10}$ is alkyl or —(CH$_2$)$_n$—C(O)R$^{11}$, is an optionally substituted phenyl group and n is 0, 1, 2, 3 or 4. Preferably, R$^{10}$ is ethyl, n-propyl or n-butyl, while R$^1$ is hydrogen or methoxy, or R$^{10}$ is 2-benzoylethyl, while R$^1$ is hydrogen.

Particularly suitable anti-hypertensive agents are those of formula 1h

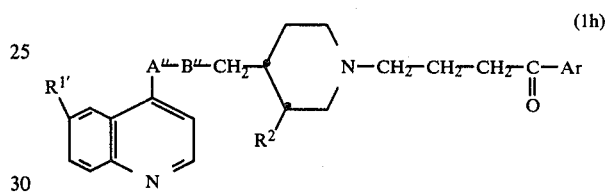

in which A″—B″ is —CHOH—CH$_2$— or —CH$_2$—CH$_2$—, R$^1$ is hydrogen or methoxy, R$^2$ is ethyl or vinyl and Ar is phenyl, thienyl or phenyl substituted by one, two or three groups, selected from fluorine, chlorine or methoxy. Especially suitable values for Ar include phenyl, fluorophenyl, chlorophenyl, methoxyphenyl, and thienyl. Most suitably A″—B″ is —CHOH—CH$_c$—. Most suitably R$^{1'}$ is hydrogen. Most suitably R$^{2'}$ is ethyl. Preferably Ar is phenyl or 4-fluorophenyl, of which 4-fluorophenyl is especially preferred. From the foregoing it will be realized that a particularly desirable anti-hypertensive compound of this invention is that of formula 1e, in which A″—B″ is —CHOH—CH$_2$—, R$^{1'}$ is hydrogen, R$^{2'}$ is ethyl and Ar is 4-fluorophenyl or phenyl.

Other particularly suitable anti-hypertensive agents are those of formula 1i

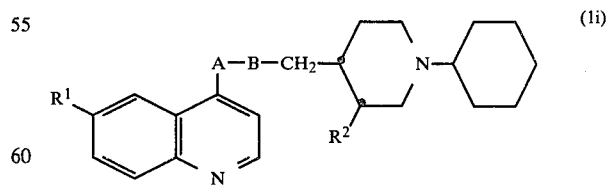

in which A—B, R$^1$ and R$^2$ are as defined above. Preferably, A—B is —CH$_2$—CH$_2$— or —CHOH—CH$_2$— or —C(O)—CH$_2$—.

Particularly suitable anti-arrhythmic compounds are those of formula 1j

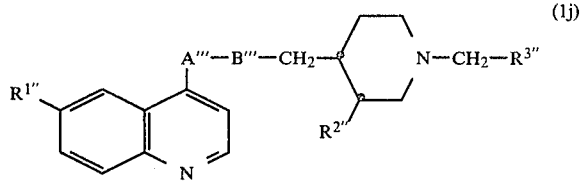

(1j)

in which A′′′—B′′′ is —CHOH—CH$_2$—, —CH$_2$—CHOH— or —CH$_2$—CH$_2$—, R$^{1''}$ is hydrogen or methoxy, R$^{2''}$ is ethyl or vinyl and R$^{3''}$ is alkyl, hydroxy alkyl or alkoxyalkyl. Most aptly A′′′—B′′′ is —CHOH—CH$_2$—. Most aptly R$^{1''}$ is methoxy. Most suitably R$^{2''}$ is ethyl. Most suitably R$^{3''}$ is ethyl. From the foregoing it will be realized that a particularly desirable anti-arrhythmic compound of this invention is that of formula 1j, in which R$^{1''}$ is methoxy and R$^{2''}$ is ethyl.

From the foregoing it will be appreciated that the following compounds according to the invention are particularly preferred:
a. N-(3-benzoylpropyl)-hydrocinchonicine
b. N-(3-benzoylpropyl)-hydrocinchonicinol-1
c. N-(3-benzoylpropyl)-desoxo-hydrocinchonicine
d. N-propyl-hydroquinicinol-1
e. N-butyl-hydroquinicinol-1
f. N-pentyl-hydroquinicinol-1
g. N-pentyl-hydrocinchonicinol-1
h. N-(4-methoxybutyl)-hydrocinchonicine.

The preceding compounds of formula 1 may exist in free base form or in the form of their acid addition or quaternary ammonium salts, for example their salts with mineral acids, e.g. hydrochloric acid, hydrobromic acid or sulphuric acid, or organic acids e.g. acetic acid, fumaric acid or tartaric acid. Naturally the acid used will be pharmaceutically acceptable.

The compounds of formula 1 in which A or B is —CHOH— contain an asymmetric carbon atom and therefore two stereoisomers may exist, provided that there are no asymmetric carbon atoms in a side chain. One or more asymmetric carbon atoms in the N-substituent may give rise to several diastereoisomeric forms.

The compounds of the invention are obtainable in crystalline form. They may also be obtained in the form of solvates such as hydrates.

The compounds of the invention, as represented by formula 1, include free base, acid addition and quaternary ammonium salt forms, racemates, separated optical forms and mixtures thereof.

The invention also provides a process for the preparation of compounds of formula 1 in which
(A) a compound of formula 5,

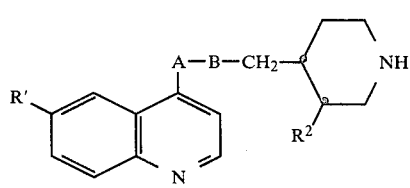

(5)

in which A—B, R$^1$ and R$^2$ are as defined above, is alkylated with a compound of formula 6,

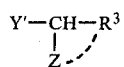

(6)

in which R$^3$ and Z are as defined above and Y′ is a nucleophilic leaving group, particularly chlorine, bromine, iodine, aryl—, aralkyl— or alkylsulphonyloxy, and especially mesyloxy or tosyloxy,
or (B) a compound of formula 7,

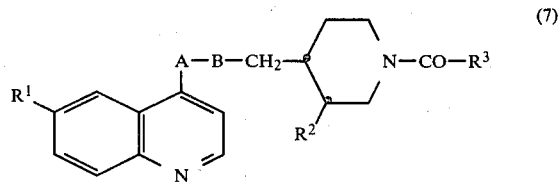

(7)

in which A—B, R$^1$ and R$^2$ are as defined above, is reduced, to give a compound of formula 1 in which Z is hydrogen,
or (C) a compound of formula 5 above is reacted with an epoxide of formula 8,

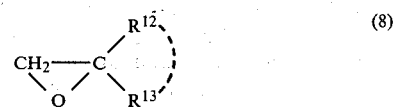

(8)

in which R$^{12}$ is C$_{1-6}$ alkyl, lower alkenyl, lower alkynyl, optionally substituted phenyl and phenyl lower alkyl and R$^{13}$ is hydrogen or lower alkyl or R$^{12}$ and R$^{13}$, together with the carbon atom to which they are attached, form a C$_{3-6}$ cycloalkyl group, to give a compound of formula 1 in which Z is hydrogen and R$^3$ is

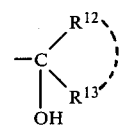

as defined above,
or (D) a compound of formula 1 in which R$^3$ contains a hydroxy group is alkylated,
or (E) a compound of formula 1 in which R$^3$ contains a hydroxy group is acylated,
or (F) a compound of formula 5 above is reacted with a compound of formula 9,

(9)

in which R$^3$ and Z are as defined above, in the presence of a reducing agent,
or (G) a compound of formula 1, in which A—B contains a carbonyl group is reacted with an O-substituted hydroxylamine derivative of formula YO-NH$_2$, in which Y is R$^4$ or a group replaceable by or convertable into R$^4$, R$^4$ being as previously defined, whereafter the resulting compound in which Y≠R$^4$ is converted in a compound in which Y=R$^4$,
or (H) a compound of formula 1 in which A—B is —C(O)—CH$_2$— or —CH$_2$—C(O)— is partially or completely reduced to —CHOH—CH$_2$— or —CH$_2$—CHOH—, or —CH$_2$—CH$_2$—, respectively.

In method A, the reaction is preferably carried out by using an equivalent amount or a small excess of the alkylation agent of formula 6. Suitably an acid binding agent is used which does not react with the alkylating agent. For this purpose sterically hindered amines, e.g. dicyclohexylethylamine can be used, but generally inorganic bases such as sodium or potassium carbonate and especially sodium or potassium bicarbonate are preferred.

The reaction is preferably carried out in an inert organic solvent, e.g. acetone, methyl ethyl ketone, methyl isobutyl ketone, tetrahydrofuran, dimethylformamide, dimethylsulphoxide, dioxane, methylene chloride, chloroform, benzene, toluene, xylene or a mixture of such solvents. Methyl ethyl ketone, dimethylformamide and toluene or mixtures thereof are preferred. Generally the reaction may be run from 0° C. to the boiling point of the solvent.

With less reactive alkylating agents the reaction can be accelerated by addition of catalytic or equivalent amounts of sodium or potassium iodide.

In method B the reduction is suitably carried out using diborane or a complex hydride, such as lithium aluminium hydride. The hydride is added in equivalent amounts or in excess, preferably in quantities up to triple the equivalent amounts. The reduction is preferably carried out in an inert solvent, in particular tetrahydrofuran, at a reaction temperature between 0° C. and the boiling point of the solvent.

It must be noted that such reducing agents will also be able to reduce carbonyl or alcohol groups. In compounds of formula 7 in which A or B is —C(O)— or —CHOH—, these groups usually will be converted into methylene groups leading to compounds of formula 1 in which A or B is reduced to —CH$_2$—.

The compounds of formula 7 may be prepared for example by acylation of a compound of formula 5 with a compound of formula 10,

(10)

in which X is halogen or —OCOR$^3$ and R$^3$ is as defined before.

The acylation of the compounds of formula 5 is preferably carried out in the presence of an acid binding agent, particularly triethylamine or pyridine. Suitable solvents include chloroform, pyridine or dimethyl formamide. Usually the reaction temperature is between 0° C. and the boiling point of the reaction mixture.

The compounds of formula 7 may also be prepared by reaction of a compound of formula 5 with a carboxylic acid of formula 10 (X is OH), in which R$^3$ is as defined above, in the presence of dicyclohexylcarbodiimide. This acylation method is effected under normal conditions, e.g. in chloroform as a solvent, after which the reaction product is isolated in a conventional manner.

Method B is advantageous for the preparation of compounds of formula 1 in which R$^3$ contains a branched alkoxyalkyl group.

Method C is suitably carried out in an inert organic solvent, preferably a lower alcohol of 1–5 carbon atoms or in a mixture of such an alcohol with dichloromethane. Sometimes it is advantageous to add water to the reaction mixture.

The reaction conditions usually depend on the reactivity of the epoxide. Usually the reaction may be run some hours and is preferably effected at temperatures in the range of 20°–120° C. Where a volatile epoxide is used, a closed system may be necessary.

In method D, the hydroxy group is suitably first converted into the corresponding alkali salt, e.g. with sodium hydride in an aprotic solvent. This salt is then treated with an alkyl halide or an alkyl or aryl sulphonic ester, preferably with an alkyl halide.

Method E is preferably carried out with an acid chloride or anhydride, as described under method B.

Method F is suitably carried out with hydrogen as reducing agent in the presence of a catalyst, for example palladium on coal. Depending on the catalyst of choice hydrogen pressures of 1–150 at are involved. The reaction conditions are as commonly used for this type of reaction. The reaction is suitably carried out in a solvent, such as a lower alcohol, preferably methanol or ethanol at a temperature generally in the range of 20°–100° C., preferably between 20°–40° C.

Another suitable method in which the use of high pressure is avoided comprises the reaction of the compounds of formulae 5 and 9 in the presence of an equivalent amount of sodium cyanoborohydride and a base, such as potassium hydroxide. The reaction is suitably carried out at room temperature, in a solvent such as an alcohol, preferably methanol or ethanol.

Method G is carried out in conventional manner for this type of reaction. Preferably, the reaction is carried out in a solvent, such as an alcohol, dioxane, dimethyl formamide, tetrahydrofuran or pyridine, at a temperature generally between room temperature and the boiling point of the reaction mixture. The hydroxylamine derivative is usually added as an acid salt, preferably the hydrochloride, which salt is preferably dissolved in pyridine. Sometimes it may be advantageous to convert the starting carbonyl compound first to, for example, the corresponding oxime. This oxime may then be converted to its sodium salt, which may be easily alkylated to the desired product.

It will be appreciated by those skilled in the art, that the conversion of the carbonyl group to the oxime ether group may occur with both the carbonyl compounds of formula 1 and formula 5.

Method H, the partial or complete reduction of a compound of formula 1, in which A—B is —C(O)—CH$_2$— or —CH$_2$—C(O)— may be carried out in conventional manner. A suitable reducing agent for the conversion to the desoxo compound (—CH$_2$—CH$_2$—) is e.g. hydrazine hydrate, in the presence of an alkali metal hydroxide, such as potassium hydroxide, in a suitable solvent such as an alcohol, e.g. ethylene glycol. A suitable reducing agent for the partial reduction to the alcohol derivative (—CHOH—CH$_2$—) is for example a complex hydride, such as sodium borohydride. This reduction is advantageously carried out at a temperature of about −5° to −10° C. in a suitable solvent, like an alcohol, preferably methanol, ethanol or isopropylalcohol. If desired, the alcohol compound may also be converted into the corresponding desoxo compound, e.g. by converting the alcohol in a suitable solvent, such as ethylalcohol, with phosphorous pentachloride to the chloride and reducing the resulting compound, for example with hydrogen gas in a solvent, such as ethylalcohol and for example palladium on coal as a catalyst.

The starting materials of formula 5 are either known or may be prepared in conventional manner from known compounds.

Compounds of formula 5, in which A—B is —C(O)—CH$_2$— may be prepared according to the methods described in French Pat. 73,41043 (publ. nr. 2,206,944) and in Dutch patent application no. 77,06614.

The methods described in said patents are based on the condensation of an ester of 3-(4-piperidyl)propionic acid with a quinoline derivative, which is substituted at the 4-position by a carboxylic ester group or a lithium atom.

In J. Amer. Chem. Soc. 100, 576–581 (1978) the preparation of a compound of formula 11

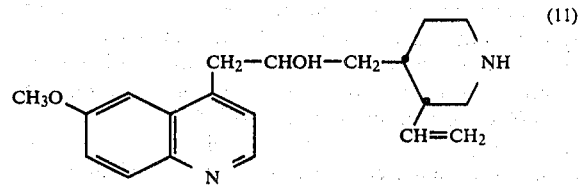

is described by converting 6-methoxylepidine in situ to 6-methoxylepidyllithium and reacting this compound with the methyl ester of a(4-piperidyl) acetic acid derivative (N-benzoylmeroquinene methyl ester). While removing the N-benzoyl group of the resulting keto compound of the 1,3-disubstituted propanone-2 type with DIBA, the compound is reduced in a propanol-2 derivative.

Compounds of formula 5 in which A—B is —CH$_2$—CHOH—, may also be prepared e.g. by reduction of a cis- or trans-oxirane compound of formula 12,

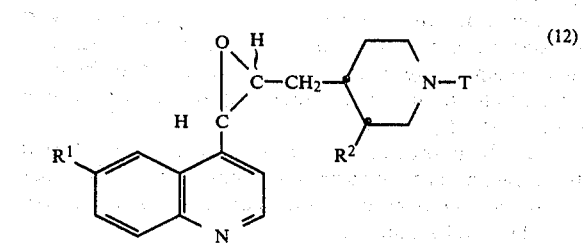

in which R$^1$ and R$^2$ are as defined above and T is a protecting group and preferably benzyl, followed by removal of this protecting group in conventional manner. The reduction is suitably carried out by leading hydrogen gas through a suitable solvent, such as an alcohol, e.g. ethylalcohol, in the presence of a suitable catalyst, e.g. palladium on coal, at room temperature or slightly elevated temperature. As a result of the reduction generally alcohols are formed as a mixture of diastereoisomers, which may be separated in conventional manner. The removal of the protecting group may be carried out with known techniques. If the protecting group is alkyl, this group may be removed e.g. with cyanogen bromide or chlorocarbonic acid ester. If the protecting group is a benzyl group, debenzylation occurs preferably catalytically.

It is noted, that the protecting group T may have the meaning of —CH$_2$R$^3$—, which is previously defined. In that case the reduction will result into a compound with formula 1, so that the removal of the protecting group may be omitted.

The preparation of the cis- and trans-oxirane compounds of formula 12 have been described by L. Keefer, Thesis Univ. of Hampshire 1966 and G. G. Lyle and L. K. Keefer, Tetrahedron 23, 3253–3263 (1967) or may be prepared in an analogous way. Generally, the compounds may suitably be prepared by quaternizing a compound of formula 13

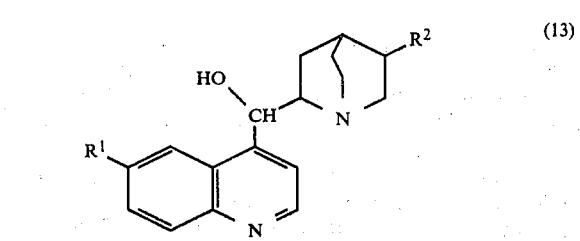

in conventional manner, for example to the corresponding benzobromide and converting the resulting compound with a base.

Because of the stereospecificity of the reaction a compound of formula 13 in the erythro configuration is preferably used as the starting material, while the quaternizing group is not too small, i.e. larger than methyl and ethyl. Thus, a suitable group is for example benzyl. The reaction with the quaternizing compound is suitably carried out with a base, such as potassium hydroxide in a solvent, such as ethylalcohol.

It is noted, that if the above-described reaction is carried out with the quaternary salt of a threo compound of formula 13, a keto compound of formula 14 may be formed,

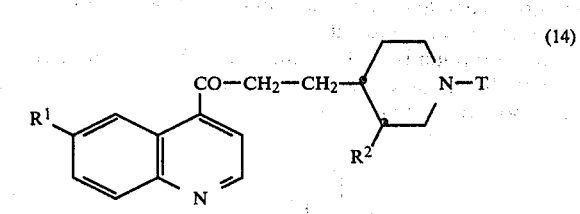

in which R$^1$, R$^2$ and T are as previously defined. If a relatively small quaternizing group is used, such as methyl group, generally a keto compound of formula 14 is formed in this reaction, both if a threo or an erythro compound of formula 9 is the starting material. Therefore, this method is also suitable for the preparation of compounds of formula 1, in which A—B is —C(O)—CH$_2$— and, after removal of the protecting group T, of the corresponding compounds of formula 5.

Threo compounds of formula 13 may also be converted to oxirane compounds of formula 12, if the quaternizing group is not too small, e.g. benzyl. This reaction is carried out with a strong base, in which B$^-$ is bulky, for example potassium t-butoxide in t-butanol. The resulting oxirane compound is usually in the cis-configuration.

The resulting compounds of formula 1 or formula 5, in which R$^1$ and R$^2$ are as previously defined and A—B is —CH$_2$—CHOH—, may be oxidized in conventional manner to the corresponding keto compounds, in which A—B is —CH$_2$—C(O)—. A suitable method includes the Oppenauer oxidation. Such keto compounds may also be prepared by the cited method described in J.

Amer. Chem. Soc. 100, 576–581 (1978), for example by condensing 4-methylquinoline which is optionally substituted at the 6-position, with the ester of a 4-piperidylacetic acid derivative under the influence of lithium and a strong base.

The reaction products from any method A—H may be isolated from the reaction mixture and purified by conventional means.

In a number of cases, certain reaction steps may be carried out in a different sequence or simultaneously or without isolating intermediates, and these possibilities are all included in the invention.

Those skilled in the art will appreciate that protecting groups may be used to protect certain reactive functions during the above processes, in accordance with conventional chemical practice.

Certain compounds of formula 1 may also be used for the preparation of other compounds of formula 1 and are therefore also suitable as intermediates.

Diastereoisomers may be separated by known techniques, based on their different physical and chemical characteristics, e.g. by fractional crystallisation or by column chromatography. These isomer separations may be effected after the final step of the synthesis used or optionally at a previous stage, after the formation of the mixture of diastereoisomers.

Racemic mixtures may be resolved into their enantiomers, in conventional manner, e.g. by separation of their salts with suitable optically active acids.

The free base and acid addition salt forms of the compounds of formula 1 may be interconverted by standard methods.

The quaternary compounds can be made by refluxing the N-substituted compounds having the desired substituent onto the piperidine-nitrogen in the presence of suitable alkyl halides. Suitable solvents for quaternisation include methanol, ethanol, tetrahydrofuran or glycerol alone or in combination with minor amounts of water, reaction temperatures varying from room temperature to the boiling point of the solvent or mixture used. Other wellknown methods such as the use of lithiumalkyl compounds or alkylmagnesium halides may be also applied. All different quaternary compounds can be made except those in which steric hindrance of the already present piperidine-substituent inhibits the formation of quaternary salts.

The compounds of formula 1 possess pharmacological activity. In particular they possess cardiovascular activity, for example anti-hypertensive, anti-thrombotic, vasodilative and anti-arrhythmic activity.

An indicated suitable daily dosage (for a 70 kg human) is from 1 to 200 mg, of a compound of formula 1, preferably administered in divided dosages of from 0.5 mg to 50 mg 2 to 4 times daily, or in retard form. Orally administrable unit dose forms may thus contain 0.5, 1, 2.5, 5, 10, 20, 25 or 50 mg of an active ingredient.

The compounds may be administered in free base form or in the form of their pharmaceutically acceptable acid addition salt forms, which salt forms have the same order of activity as the free base forms.

The compounds of formula 1 may be admixed with conventional pharmaceutically acceptable diluents or carriers and, optionally, other excipients, and administered for example in such forms as tablets, capsules and injectable solutions. They may also be administered in combination preparations with other active agents.

The pharmaceutical compositions may be formulated in conventional manner, e.g. as for other anti-hypertensive agents.

The invention also relates to a method for the preparation of a pharmaceutical composition, characterized in that at least a compound of formula 1, as defined hereinbefore, or a pharmaceutically acceptable salt thereof, is brought in a form suitable for therapeutic purposes.

The invention further relates to a method of treating mammals, in particular humans, suffering from e.g. cardiovascular diseases, which comprises administering an effective amount of a compound of formula 1 as defined hereinbefore or a pharmaceutically acceptable salt thereof, preferably in the form of a pharmaceutical composition.

The following Examples illustrate the invention.

EXAMPLE 1

N-(3-benzoylpropyl)-hydrocinchonicine

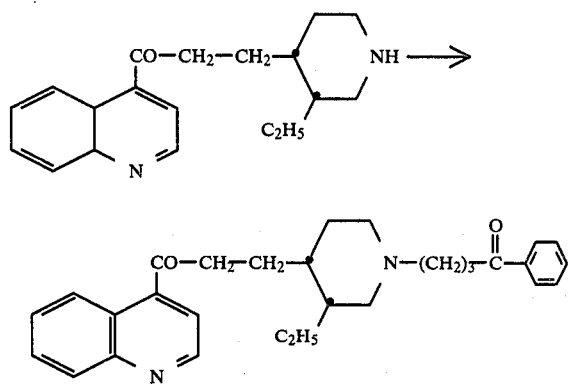

A solution of 249.3 g (0.75 mole) of hydrocinchonicine HCl in 2000 ml of water was made alkaline with 4N sodium hydroxide (pH 9-10) and extracted with 1000 ml of toluene. The water phase was separated from the toluene and the toluene phase was dried over mol. sieves (4 Å) and filtered.

To the dried solution 207 g (1.5 mole) of potassium carbonate and 164.3 g (0.9 mole) of γ-chlorobutyrophenone were added, and the mixture was refluxed for 24 hours with stirring. A precipitate of potassium chloride was formed during the reaction. The conversion was followed by thin-layer chromotography (silica gel with chloroform/acetone/diethyl amine 5:4:1 as the eluent). After the reaction mixture was cooled to room temperature water was added, the layers were separated and the toluene phase concentrated in vacuo to about 250 ml. The solution was filtered over a short silica gel column, chloroform being the eluent. The fractions with the desired product were evaporated to dryness in vacuo and the title compound remained as an oil.

EXAMPLE 2

N-(3-benzoylpropyl)-hydrocinchonicine bifumarate

The oil obtained according to Example 1 was dissolved in acetone. Fumaric acid was then added to the boiling solution till pH 6-7 was reached. Upon cooling to room temperature, the title compound crystallized. The salt was recrystallized from actone/methanol, melting point 127°-129° C.

In the same way the following compounds were prepared:

$$R^1 \underset{N}{\text{quinoline}}{-}A{-}CH_2{-}CH_2{-}\underset{R^2}{\text{piperidine}}{-}NH + QX \longrightarrow$$

$$R^1 \underset{N}{\text{quinoline}}{-}A{-}CH_2{-}CH_2{-}\underset{R^2}{\text{piperidine}}{-}N{-}Q \quad (+ HX)$$

| Ex | A | R$^1$ | R$^2$ | Q | m.p. °C./salt | X |
|---|---|---|---|---|---|---|
| 1 (rep.) | CO | H | ethyl | —(CH$_2$)$_3$—CO—C$_6$H$_5$ | (oil) | Cl |
| 2 (rep.) | CO | H | ethyl | —(CH$_2$)$_3$—CO—C$_6$H$_5$ | 127–129 BF | Cl |
| 3 | CO | OCH$_3$ | vinyl | —(CH$_2$)$_3$—CO—C$_6$H$_5$ | 117–119 BF | Cl |
| 4 | CHOH | H | ethyl | —(CH$_2$)$_3$—CO—C$_6$H$_5$ | 184–186 BO | Cl |
| 5 | CHOH | OCH$_3$ | ethyl | —(CH$_2$)$_3$—CO—C$_6$H$_5$ | 148–151 BO | Cl |
| 6 | CH$_2$ | H | vinyl | —(CH$_2$)$_3$—CO—C$_6$H$_5$ | 119–121 BF | Cl |
| 7 | CH$_2$ | H | ethyl | —(CH$_2$)$_3$—CO—C$_6$H$_5$ | 191–192 BO | Cl |
| 8 | CH$_2$ | OCH$_3$ | vinyl | —(CH$_2$)$_3$—CO—C$_6$H$_5$ | 92–94 HCl | Cl |
| 9 | CO | H | ethyl | —(CH$_2$)$_3$—CO—C$_6$H$_4$—CH$_3$ | 121–123 BF | Cl |
| 10 | CH$_2$ | H | vinyl | —(CH$_2$)$_3$—CO—C$_6$H$_4$—CH$_3$ | 124–126 BF | Cl |

-continued $$R^1 \text{-quinolin-4-yl} - A - CH_2 - CH_2 - \overset{R^2}{\underset{}{\text{piperidinyl}}} - NH + QX \longrightarrow$$

$$R^1 \text{-quinolin-4-yl} - A - CH_2 - CH_2 - \overset{R^2}{\underset{}{\text{piperidinyl}}} - N - Q \quad (+ HX)$$

| Ex | A | $R^1$ | $R^2$ | Q | m.p. °C./salt | X |
|----|------|------|-------|-----------------------------|------------------------|----|
| 11 | CO | H | ethyl | $-(CH_2)_3-CO-$C_6H_4$-OH | 175–177 Fu | Cl |
| 12 | CO | H | ethyl | $-(CH_2)_3-CO-$C_6H_4$-OCH_3 | 139–141 BF | Cl |
| 13 | $CH_2$ | H | ethyl | $-(CH_2)_3-CO-$C_6H_4$-OCH_3 | 122–124 BF | Cl |
| 14 | CO | H | ethyl | $-(CH_2)_3-CO-$C_6H_4$-Cl | 128–130 BF | Cl |
| 15 | $CH_2$ | $OCH_3$ | vinyl | $-(CH_2)_3-CO-$C_6H_4$-Cl | 128–131 biHCl | Cl |
| 16 | CO | H | ethyl | $-(CH_2)_3-CO-$C_6H_4$-F | 143–146 BF | Cl |
| 17 | CHOH | H | ethyl | $-(CH_2)_3-CO-$C_6H_4$-F | 186–188 BO | Cl |
| 18 | CHOH | H | ethyl | $-(CH_2)_3-CO-$C_6H_4$-F | 183–185 BO (one isomer) | I |
| 19 | $CH_2$ | H | ethyl | $-(CH_2)_3-CO-$C_6H_4$-F | 196–198 BO | I |
| 20 | $CH_2$ | $OCH_3$ | ethyl | $-(CH_2)_3-CO-$C_6H_4$-F | 182–183 BO | I |

-continued

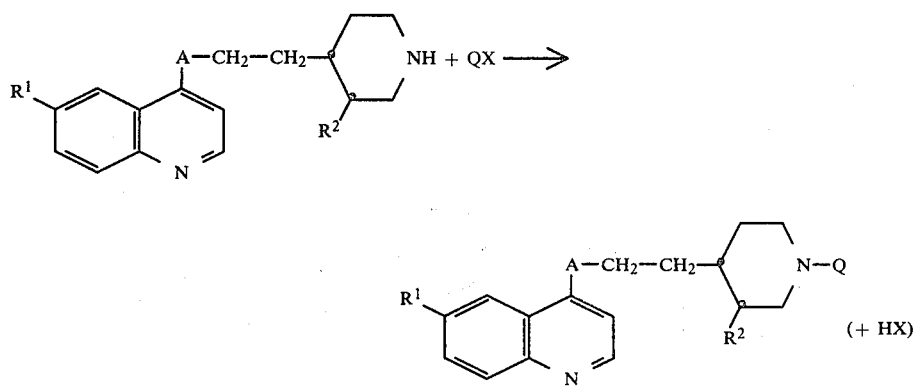

| Ex | A | R¹ | R² | Q | m.p. °C./salt | X |
|----|---|----|----|---|---------------|---|
| 21 | CH₂ | OCH₃ | vinyl | —(CH₂)₃—CO—C₆H₄—F | 151–152 BO | I |
| 22 | CHOH | OCH₃ | vinyl | —(CH₂)₃—CO—C₆H₄—F | 159–161 (d) TO (2:3) | I |
| 23 | CO | H | ethyl | —(CH₂)₃—CO—C₆H₃Cl₂ | 122–124 BF | Cl |
| 24 | CO | H | ethyl | —(CH₂)₃—CO—(thienyl) | 157–160 BF | Cl |
| 25 | CO | H | ethyl | —(CH₂)₂—CH₃ | 187–189 BO | Br |
| 26 | CHOH | OH | ethyl | —(CH₂)₂—CH₃ | 134–137 TO (2:3) | Br |
| 27 | CO | OH | ethyl | —(CH₂)₂—CH₃ | 158–159 HCl | Br |
| 28 | CO | OCH₃ | ethyl | —(CH₂)₂—CH₃ | 202–204 BO | Br |
| 29 | CO | OC₃H₇ | ethyl | —(CH₂)₂—CH₃ | 135–136 BF | Br |
| 30 | CO | O—iC₅H₁₁ | ethyl | —(CH₂)₂—CH₃ | 190–192 BO | Br |
| 31 | CHOH | OCH₃ | ethyl | —(CH₂)₂—CH₃ | 124 (d) HCl | Br |
| 32 | CHOH | OCH₃ | ethyl | —(CH₂)₂—CH₃ | 136–138 base (one isomer) | Br |
| 33 | CH₂ | H | vinyl | —(CH₂)₂—CH₃ | 236–239 biHCl | Br |
| 34 | CH₂ | H | ethyl | —(CH₂)₂—CH₃ | 178–180 HCl | Br |
| 35 | CH₂ | OH | ethyl | —(CH₂)₂—CH₃ | 176–179 HCl | Br |
| 36 | CH₂ | OCH₃ | ethyl | —(CH₂)₂—CH₃ | 145–153 BO | Br |
| 37 | CH₂ | OC₃H₇ | ethyl | —(CH₂)₂—CH₃ | 136–138 BO | Br |
| 38 | CH₂ | O—iC₅H₁₁ | ethyl | —(CH₂)₂—CH₃ | 158–159 BO | Br |
| 39 | CO | H | ethyl | —(CH₂)₃—CH₃ | 160–162 BF | Br |
| 40 | CHOH | OCH₃ | ethyl | —(CH₂)₃—CH₃ | 115–118 TO (2:3) | Br |
| 41 | CO | H | eythyl | —(CH₂)₄—CH₃ | 102–104 BF | Br |
| 42 | CHOH | H | ethyl | —(CH₂)₄—CH₃ | 116–119 BO | Br |
| 43 | CH₂ | H | vinyl | —(CH₂)₄—CH₃ | 142–143 BO | Br |
| 44 | CH₂ | H | ethyl | —(CH₂)₄—CH₃ | 141–142 BF | Br |
| 45 | CHOH | OCH₃ | ethyl | —(CH₂)₄—CH₃ | 106–108 base | Br |
| 46 | CH₂ | OCH₃ | vinyl | —(CH₂)₄—CH₃ | 80–83 BO | Br |
| 47 | CH₂ | OCH₃ | ethyl | —(CH₂)₄—CH₃ | 145–147 BO | Br |
| 48 | CO | H | ethyl | —(CH₂)₅—CH₃ | 106–108 BF | Br |
| 49 | CO | H | ethyl | —(CH₂)₆—CH₃ | 90–93 BF | Br |
| 50 | CO | H | ethyl | —(CH₂)₈—CH₃ | 105–107 BF | Br |
| 51 | CO | OCH₃ | vinyl | —(CH₂)₈—CH₃ | 134–136 BF | Br |
| 52 | CH₂ | H | vinyl | —(CH₂)₈—CH₃ | 173–174 BO | Br |
| 53 | CH₂ | OH | ethyl | —(CH₂)₈—CH₃ | 156–158 BO | Br |
| 54 | CH₂ | OCH₃ | vinyl | —(CH₂)₈—CH₃ | 135–137 BO | Br |
| 55 | CO | H | ethyl | —CH₂—CH(CH₃)₂ | 148–150 BF | Br |
| 56 | CO | H | ethyl | —(CH₂)₂—CH(CH₃)₂ | 180–182 BF | Br |
| 57 | CH₂ | OCH₃ | ethyl | —(CH₂)₂—CH(CH₃)₂ | 134 BO | Br |
| 58 | CO | H | ethyl | —(CH₂)₃—CH(CH₃)₂ | 138–140 BF | Br |

-continued

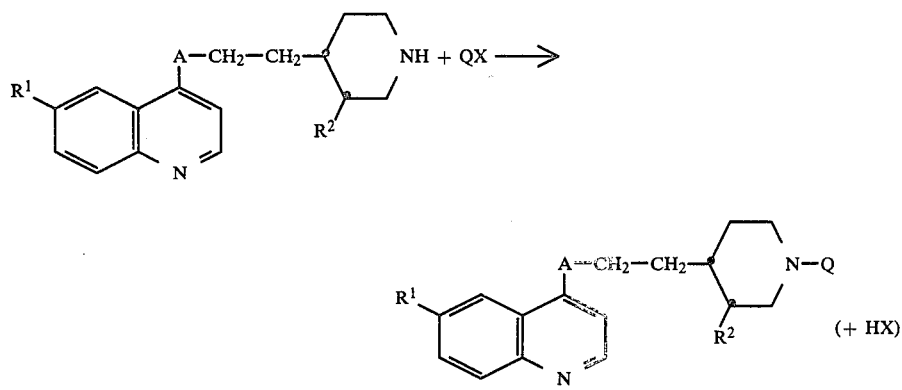

| Ex | A | R¹ | R² | Q | m.p. °C./salt | X |
|---|---|---|---|---|---|---|
| 59 | CO | OCH₃ | vinyl | —CH₂—CH₂—(cyclohexyl) | 183–185 BF | I |
| 60 | CO | H | ethyl | —(CH₂)₃—CH₂OH | 140–143 BO | Br |
| 61 | CO | H | ethyl | —CH₂—CH₂—(OH)C—(CH₃)₂ | 142–145 BO | Br |
| 62 | CO | H | ethyl | —CH₂—CH₂—OCH₃ | 140–142 BF | Br |
| 63 | CO | OCH₃ | vinyl | —CH₂—CH₂—OCH₃ | 126–128 BF | Br |
| 64 | CO | H | ethyl | —(CH₂)₃—O—CH₃ | (oil) | |
| 65 | CHOH | H | ethyl | —(CH₂)₄—OCH₃ | 144–148 BO | Br |
| 66 | CO | H | ethyl | —(CH₂)₄—OCH₃ | 108–110 BF | Br |
| 67 | CO | H | ethyl | —(CH₂)₄—CN | 149–151 BO | Br |
| 68 | CO | H | ethyl | —CH₂—(cyclopropyl) | 201 BO | Br |
| 69 | CO | H | ethyl | —CH₂—(tetrahydrofuran-2-yl) | 146 (d) BF | Br |
| 70 | CO | H | ethyl | —(CH₂)₂—N(CH₃)₂ | (oil) | Cl |
| 71 | CO | H | ethyl | —CH₂CHOHCH₂—N(C₂H₅)₂ | 122–125 TO | Cl |
| 72 | CO | OCH₃ | vinyl | —CH₂—CH=CH₂ | 97–99 BF | Cl |
| 73 | CH₂ | OCH₃ | vinyl | —CH₂—CH=CH₂ | 191–193 Pa | Cl |
| 74 | CH₂ | OCH₃ | ethyl | —CH₂—CH=CH₂ | 145–148 BO | Cl |
| 75 | CO | H | ethyl | —CH₂—CH=CH—(phenyl) | 153–144 BF | Br |
| 76 | CO | H | ethyl | —CH₂—C≡CH | 203–205 BO | Cl |
| 77 | CO | H | ethyl | —CH₂—CH₂—(3,4-dimethoxyphenyl) | 170–172 BF | Br |
| 78 | CO | H | ethyl | —CH₂—CH₂—(3,4,5-trimethoxyphenyl) | 155–160 (d) TO (2:3) | Br |
| 79 | CO | H | ethyl | —(CH₂)₃—CH(4-F-C₆H₄)₂ | 170 (d) HCl | Cl |

-continued

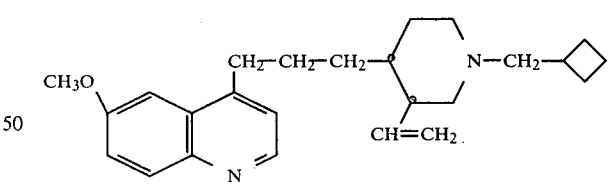

| Ex | A | R¹ | R² | Q | m.p. °C./salt | X |
|---|---|---|---|---|---|---|
| 80 | CH₂ | OCH₃ | vinyl | —(CH₂)₃—CH—[C₆H₄—F]₂ | 124 (d) HCl | Cl |
| 81 | CO | OCH₃ | vinyl | —CH₂CO—C₆H₅ | 150–152 BO | Br |
| 82 | CO | H | ethyl | —(CH₂)₂—CO—C₆H₄—F | 153–155 BF | Br |
| 83 | CO | H | ethyl | —(CH₂)₄—CO—C₆H₄—F | 175–178 BO | I |
| 84 | CO | H | ethyl | —(CH₂)₃—CHOH—C₆H₄—F | 189–192 BO | I |

The salts in the Table have been abbreviated as follows:
BF=bifumarate
BO=bioxalate
Fu=fumarate
Pa=pamoate
TO=trioxalate The compounds mentioned in the Table are all Examples which illustrate the invention. For clarity's sake the compounds prepared according to Examples 1 and 2 have also been mentioned in the Table.

EXAMPLE 85

N-cyclobutylmethyl-desoxoquinicine hydrochloride

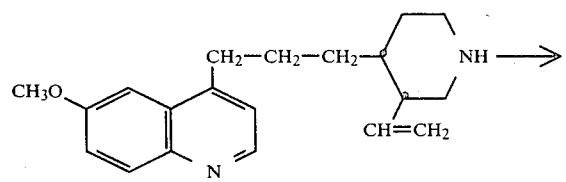

To a suspension of 10.0 g (28.8 mmole) of desoxoquinicine.HCl in 125 ml of dichloromethane 58 ml of triethylamine was added with stirring.

In 60 ml of dichloromethane 8.6 g (86.4 mmole) of cyclobutanecarboxylic acid was dissolved, then 10.3 g (86.4 mmole) of thionyl chloride was dropwise added with stirring and the solution was refluxed for 1 h. After cooling to room temperature the resulting solution was dropwise added to the above-mentioned solution of desoxoquinicine in dichloromethane with stirring in a nitrogen atmosphere. The solution was refluxed with stirring for another 2 hours. The reaction mixture was cooled to room temperature and 1000 ml of water was added with stirring.

The layers were separated and the water layer was extracted twice with 50 ml of chloroform. The combined extract of dichloromethane and chloroform was shaken twice with 100 ml of water, dried over magnesium sulphate, filtered and evaporated in vacuo. The residue was chromatographed over silica gel with chloroform/acetone/diethylamine 5:4:1 as the eluent. The fractions containing the acid amide were collected and evaporated to dryness in vacuo. The residue was dissolved in 450 ml of dry tetrahydrofuran and dropwise added to a suspension of 3.2 g (86.4 mmole) of lithium aluminum hydride in 120 ml of dry tetrahydrofuran with stirring in a nitrogen atmosphere. Stirring was continued for another 2 hours followed by refluxing for 1 hour.

The solution was cooled to room temperature and 40 ml of ethyl acetate was dropwise added with stirring and cooling in ice water, followed by 300 ml of a 30% solution of ammonium chloride. The organic phase was separated, dried over magnesium sulphate, filtered and evaporated to dryness in vacuo.

The residue was chromatographed over silica gel with cyclohexane/acetone 8:1 as the eluent. The fractions containing the N-cyclobutylmethyldesoxoquinicine were evaporated to dryness in vacuo, then the base was converted to the HCl-salt with 1 eq. of isopropylalcohol.HCl. Melting point 140°–143° C.

EXAMPLE 86

N-(2-hydroxy-2-methylpropyl)-hydrocinchonicine bioxalate (formula: see table below)

To a solution of 22g of hydrocinchonicine in 80 ml of absolute alcohol 9 ml of 1,2-epoxy-2-methylpropane was added. The mixture was refluxed for 2 hours and the conversion was followed by thin layer chromatography. The reaction mixture was cooled to room temperature and evaporated to dryness in vacuo.

The residue was purified by preparative high pressure liquid chromatography with ethyl acetate/diethyl amine 95:5 as the eluent. The fractions containing the purified product were collected and evaporated to dryness in vacuo. The residue was dissolved in ethyl acetate/methanol. The solution was heated, then the base was converted into the bioxalate (1:1) with an equivalent amount of oxalic acid. Melting point 132°–134° C.

In a similar way the following compounds have been obtained which are mentioned (next to the compound described in this Example) in the table below:

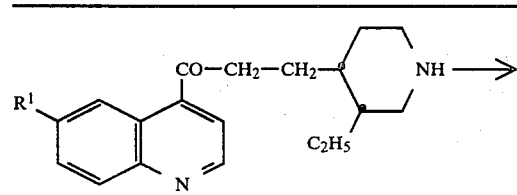

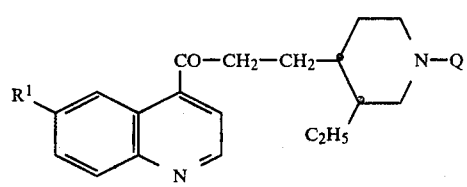

| Ex | R¹ | Q | m.p. (°C.) salt |
|---|---|---|---|
| 86 | H | —CH₂C(OH)(CH₃)₂ | 132–134 bioxalate |
| (rep.) 87 | H | —CH₂C(OH)(C₂H₅)₂ | 72–75 bioxalate |
| 88 | H | —CH₂CH(OH)—⌬ | 163–165 bioalate |
| 89 | H | —CH₂—▷ OH | 172–174 bioxalate |
| 90 | H | —CH₂—▱ OH | 82–85 bioxalate |
| 91 | H | —CH₂—C(OH)(CH₃)—⌬ | 228–229 HBr |

EXAMPLE 92

N-Cyclohexyl-hydrocinchonicineoxalate

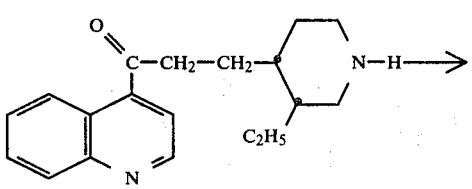

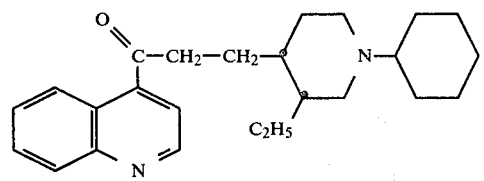

To a solution of 50 ml of methanol with 0.5 g of potassium hydroxide was added with stirring 6.7 g (0.020 mol) of hydrocinchonicinehydrochloride. After stirring for some time 1.96 g (0.020 mol) of cyclohexanone was added. Then 0.44 g (0.007 mol) of sodium cyanoborohydride was added and the reaction mixture was stirred for 30 min. at room temperature. After adding 0.5 g potassium hydroxide stirring was continued for 4h. at room temperature. The reaction mixture was evaporated to dryness in vacuo and treated with ether and water. The ether layer was extracted with 4 n HCL. The water layer was basified with 4 n sodium hydroxide and extracted with ether. The ether extract was dried on magnesium sulfate, filtered and evaporated to dryness in vacuo. The crude product was purified over Silica Gel G with ethylacetate/diethylamine (9:1) as eluent.

With oxalic acid the base was converted to its oxalate (mol. ratio 1:1.25) having a melting point of 108°-109° C.

In the same way were prepared:

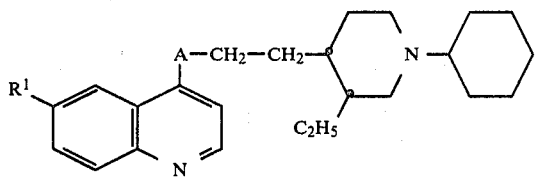

| Ex | A | R¹ | m.p. (°C.) | salt |
|---|---|---|---|---|
| 92 (rep.) | CO | H | 108-109 | BO |
| 93 | $CH_2$ | H | 101-104 | BO |
| 94 | CHOH | H | 198-200 | BO |
| 95 | $CH_2$ | $OCH_3$ | 69-70 | base |

EXAMPLE 96

1-(6-methoxy-4-quinolyl)-3-[3(R)-ethyl-N-propyl-4-(S)-piperidyl]-propanone-2

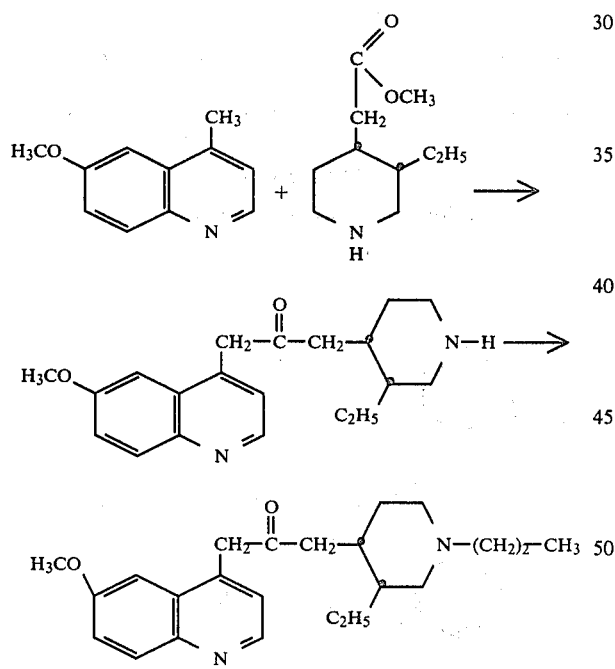

To 46.6 ml (77.2 mmol) of a 15%-solution of n-butyl lithium in hexane was added under nitrogen 9.2 g (91.1 mmol) of diisopropylamine with stirring at −5° to −10° C. over 20 min. Then 11.75 g (67.9 mmol) of 6-methoxylepidine in 40 ml of tetrahydrofuran was added dropwise with stirring at −5° C. followed by dropwise addition of a solution of 7.6 g (41.1 mmol) of [3 (R)-ethyl-4(S)-piperidyl] acetic acid methyl ester in 40 ml of tetrahydrofuran. Stirring was continued at −5° C. for 3 h.

The reaction mixture was acidified (pH 6 with acetic acid and 5 g of potassium bicarbonate was added. Then the reaction mixture was diluted with 100 ml of methanol, filtered and evaporated to dryness in vacuo. To the residue 150 ml of water and 4 n HCL was added to pH 4. Then the mixture was extracted with ether (total volume of 350 ml).

The water layer was basified with concentrated ammonia to pH 8-9 and extracted with toluene (total volume of 200 ml). The toluene extract was dried over magnesium sulfate, filtered and evaporated to dryness in vacuo.

This crude 1-(6-methoxy-4-quinolyl)-3-[3 (R)-ethyl-4 (S)-piperidyl]-propanone-2 was dissolved in 80 ml of dimethyl formamide and 6.1 g (61.2 mmol) of propyl iodide in 40 ml of dimethyl formamide was added with stirring.

The reaction mixture was heated to 50°-60° C. and stirred for 2h.

The reaction mixture was poured into 500 ml of water and extracted with toluene (total volume of 450 ml). The toluene extract was dried over magnesium sulfate, filtered and evaporated to dryness in vacuo. The crude product was purified over Silica Gel G with ethylacetate containing 5% diethylamine as eluent.

The 1-(6-methoxy-4-quinolyl)-3-[3(R)-ethyl-N-propyl-4 (S)-piperidyl]-propanone-2 was obtained as an oil.

EXAMPLE 97

1-(6-methoxy-4-quinolyl)-3-[3(R)-ethyl-N-propyl-4(S)-piperidyl]-propanol-2.

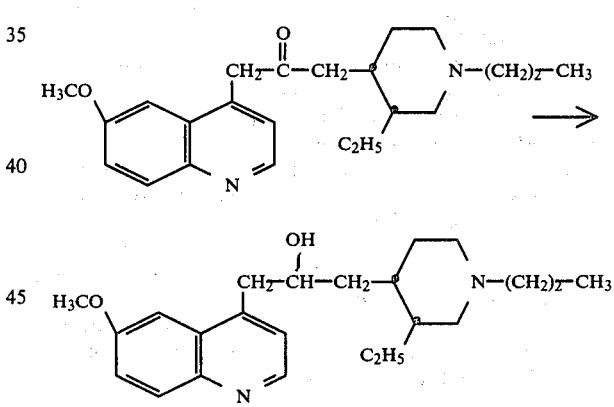

A mixture of 9.0 g (24.5 mmol) 1-(6-methoxy-4-quinolyl)-3-[3(R)-ethyl-N-propyl-4(S)-piperidyl]-propanone-2 and 0.6 g (15.9 mmol) of sodiumborohydride in 75 ml of methanol containing 0.5 ml of a 4 n sodiumhyroxide solution and 9 ml of water was stirred at room temperature for 3 h. Then 150 ml of water was added and the mixture was extracted with chloroform (total volume of 300 ml). The chloroform extract was dried over magnesium sulfate, filtered and evaporated to dryness in vacuo.

The crude product was purified over Silica Gel G with ethylacetate containing 5% diethylamine as eluent.

The 1-(6-methoxy-4-quinolyl)-3-[3(R)-ethyl-N-propyl-4 (S)-piperidyl]-propanol-2 (mixture of isomers) was obtained as an oil. Melting point of hydrobromide salt is 213° C.

EXAMPLE 98

N-propyl-hydrocinchonicine-O-methyl oxime bioxalate

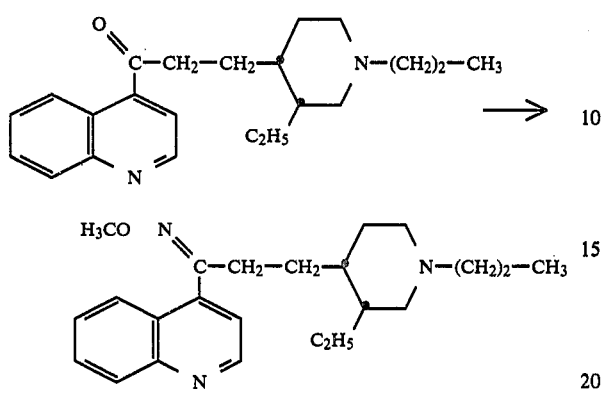

A mixture of 23.0 g (0.068 mol) of N-propyl-hydrocinchonicine (25) and 8.0 g (0.096 mol) of methoxylamine in 200 ml of absolute ethanol was refluxed for 16 h.

After cooling to room temperature the reaction mixture was evaporated to dryness in vacuo. Water was added to the residue, the mixture basified with concentrated ammonia and extracted with chloroform. The chloroform extract was dried over magnesium sulfate, filtered and evaporated to dryness in vacuo.

The crude product was purified over Silica Gel G with ethylacetate/diethylamine (50:1) as eluent. The N-propyl-hydrocinchonicine-O-methyl oxime (mixture of isomers) was obtained as an oil.

With oxalic acid the base was converted to the oxalate (mol. ratio 1:1.25) with a melting point of 154° C.

EXAMPLE 99

N-(2-methyl-2-propionyloxypropyl)-hydrocinchonicine bifumarate

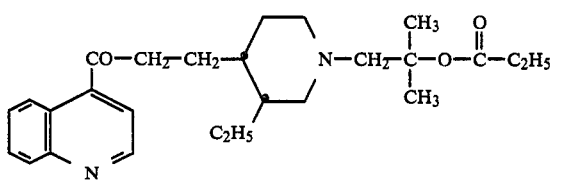

A mixture of 15.0 g (40 mmole) of N-(2-hydroxy-2-methylpropyl)-hydrocinchonicine, 4.4 g (48 mmole) of propionyl chloride and 5.7 g (56 mmole) of triethyl amine in 300 ml of carbon tetrachloride was refluxed overnight with stirring. The reaction mixture was cooled to room temperature and evaporated to dryness in vacuo. The residue was dissolved in 100 ml of toluene and subsequently extracted with 25 ml of water, 25 ml of a saturated solution of sodium bicarbonate and 25 ml of water. The layers were separated and the organic layer was dried over magnesium sulphate, filtered and concentrated in vacuo.

The residue was dissolved in 50 ml of cyclohexane and chromatographed over a silica gel column with cyclohexane/acetone 3:1 as the eluent. The fraction containing the desired product was evaporated to dryness in vacuo, then the base was dissolved in 25 ml of acetone. To the solution 1.6 g of fumaric acid in isopropylalcohol was added. The salt obtained was isolated and recrystallized from methanol/ethyl acetate. Melting point 132°–134° C.

EXAMPLE 100

N-propyl-hydroquinicine-methoiodide.

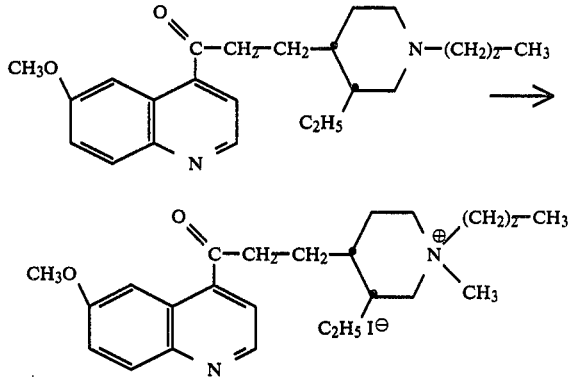

10 grams (27 mmol) of N-propyl-hydroquinicine was dissolved in 150 ml of 96% ethylalcohol, to which mixture 5 grams (35 mmol) of methyliodide were added.

The mixture was gently heated under reflux until all of the starting material had been consumed; the reaction was followed by means of TLC.

After completion of the reaction the reaction mixture was evaporated to dryness in vacuo and recrystallized from an ethylalcohol-water mixture, containing 30% of water. The desired methiodide was obtained after filtration and drying in vacuo. The melting point of N-propyl-hydroquinicine-methoiodide after recrystallisation was 180°–185° C.

PHARMACOLOGY

Experiment 1

Effectiveness of the compounds of Examples in spontaneously hypertensive rats

Systolic blood pressures were recorded by a modification of the tail cuff method described I. M. Claxton et al, Eur. J. Pharmacology 37, 179 (1976). An oscilloscope or W+W BP recorder, model 8002, was used to display pulses.

Prior to all measurements rats were placed in a heated environment (33.5°±0.5° C.) before transfer to a restraining cage. Each determination of blood pressure was the mean of at least 6 readings.

Spontaneously hypertensive rats (aged 12–18 weeks) with systolic blood pressures >170 mm Hg were considered hypertensive. Groups of 6 animals (n=6) were used unless specified.

In the following Table the results with certain compounds of the invention, which have been carried out with the above-described method, are mentioned. The numbers of the compounds correspond with those of the Examples.

TABLE 1

| Compound No. | dosage mg/kg | change of systolic blood pressures (%) in different time intervals (h) | | | | |
|---|---|---|---|---|---|---|
| | | 1 | 2 | 4 | 6 | 24 |
| 2 | 100 | −20 | −27 | −17 | −15 | +3 |
| 4 | 10 | −34 | −25 | −23 | −21 | −4 |
| 6 | 10 | 0 | −2 | −14 | −15 | −7 |

TABLE 1-continued

| Compound No. | dosage mg/kg | change of systolic blood pressures (%) in different time intervals (h) | | | | |
|---|---|---|---|---|---|---|
| | | 1 | 2 | 4 | 6 | 24 |
| 7 | 10 | −26 | −27 | −36 | −28 | +4 |
| 8 | 100 | −27 | −40 | −39 | −10 | −4 |
| 11 | 10 | 0 | 1 | −1 | −6 | — |
| 12 | 100 | −28 | −38 | −23 | 0 | 0 |
| 14 | 100 | −10 | −9 | −3 | 1 | −1 |
| 16 | 10 | −28 | −30 | −38 | −30 | −7 |
| 17 | 10 | −38 | −35 | −34 | −32 | +1 |
| 18 | 1 | −6 | −11 | −14 | −9 | +17 |
| 19 | 10 | −8 | −17 | −23 | −30 | 9 |
| 20 | 10 | −37 | −34 | −33 | −27 | 0 |
| 21 | 10 | −41 | −24 | −26 | −25 | −13 |
| 22 | 1 | −13 | −11 | −12 | −11 | — |
| 24 | 10 | −5 | −16 | −14 | −15 | −5 |
| 25 | 100 | −12 | −24 | −28 | −25 | +1 |
| 28 | 10 | 3 | −5* | −4 | −19* | −1 |
| 29 | 10 | −8 | −10 | −12 | −16 | +2 |
| 30 | 100 | −23 | −34 | −35 | −48 | −17 |
| 31 | 10 | −3 | −2 | −11 | −15 | −3 |
| 34 | 100 | −24 | −37 | −29 | −48 | −2 |
| 41 | 100 | −17 | −34 | −37 | −34 | −3 |
| 42 | 100 | −38 | −35 | −40 | −25 | +3 |
| 44 | 100 | −25 | −19 | −18 | −29 | −2 |
| 60 | 10 | −4 | −11 | −8 | −13 | — |
| 66 | 100 | −7 | −13 | −20 | −13 | −3 |
| 67 | 10 | −11 | −13 | −14 | −20 | −5 (n = 5) |
| 68 | 10 | −9 | 3 | −5 | −2 | 2 (n = 4) |
| 70 | 10 | +1 | +2 | −3 | −11 | +2 |
| 71 | 10 | −3 | −6 | −8 | −5 | +8 |
| 80 | 100 | −17 | −28 | −44 | −44 | −7 |
| 82 | 100 | −22 | −14 | −23 | −12 | +4 |
| 83 | 10 | 0 | −9 | −12 | −10 | 12 |
| 84 | 10 | −6 | −28 | −10 | −19 | +2 |
| 86 | 100 | +2 | −7 | −2 | −13 | +8 |
| 88 | 100 | −9 | −15 | −23 | −9 | +14 |
| 89 | 10 | −1 | −7 | −14 | −14 | −5 |
| 90 | 10 | −3 | −5 | −7 | −9 | −11 |
| 92 | 10 | −1 | −5 | −22 | −23* | −3 (n = 5) |
| 93 | 100 | −11 | −14 | −17 | −20 | 3 |
| 94 | 10 | −9 | −11 | −12 | −16 | 0 |
| 95 | 100 | −16 | −23 | −35 | −23 | +5 |

*No pulse in 2 rats

Experiment 2

Effectiveness of the compounds of Examples in the Guinea Pigs Electrostimulation Test Arrhythmias were induced in guinea pigs by electrostimulation of the right ventricle of the heart. The animals were anaesthetisized with urethane (1.2 g/kg i.p.) and artificially respirated before a needle electrode was inserted in the right ventricle of the heart. Substances were given intraduodenally 30 min. before the stimulation at a dose of 32 mg/kg.

The voltage needed for induction of extra systoles in control animals (n=6) was compared with that required for induction of arrhythmias in treated animals (n=6).

This method is based on the work of L. Szekeres and G. J. Papp, Naunyn-Schmiedebergs Arch. Exp. Path. Pharmak., 245, 70 (1963).

In the Table the results of certain compounds of the invention are mentioned, which have been carried out according to the method described above.

The numbers of the compounds correspond with those of the Examples.

TABLE 2

| Compound Number | Percent Increase in Voltage (%) Required for Arrhythmia |
|---|---|
| 2 | 46 |
| 4 | 5 |
| 6 | Ia* |
| 7 | 9 |
| 11 | 12 |
| 24 | Ia* |
| 25 | 48 |
| 26 | 11 |
| 27 | 6 (16) |
| 30 | 25 |
| 31 | 141 |
| 32 | 121 |
| 35 | 20 (16) |
| 38 | 20 |
| 40 | 85 |
| 41 | 30 |
| 42 | 28 |
| 45 | 72 |
| 53 | 15 (16) |
| 57 | 9 |
| 66 | 18 |
| 67 | Ia* |
| 68 | 15 |
| 70 | Ia* |
| 71 | 23 |
| 86 | 56 |
| 89 | 9 |
| 92 | Ia* |
| 98 | 58 |
| 100 | 51 (16) |

*Inactive at the tested dosage.

Guinea Pig Electrostimulation Test at 32 mg/kg unless Indicated in Brackets after Result Some compounds also showed anti-depressant activity and some compounds also showed anti-inflammatory activity, in preliminary tests.

We claim:
1. A compound of formula 1 or a pharmaceutically acceptable salt thereof.

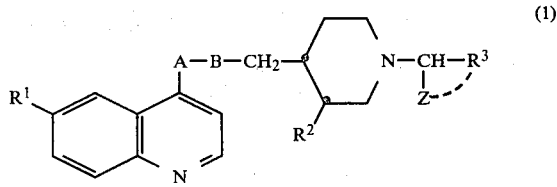

(1)

in which
A—B is —CH$_2$—CH$_2$—, —CHOH—CH$_2$—, —CH$_2$—CHOH—, —C(O)—CH$_2$—, —CH$_2$—C(O)—, —C(-NOR$^4$)—CH$_2$— or —CH$_2$—C(NOR$^4$)—,
R$^1$ is hydrogen, hydroxy or lower alkoxy,
R$^2$ is ethyl or vinyl,
R$^3$ is C$_{2-8}$ alkyl, C$_{1-8}$ hydroxyalkyl, lower alkoxyalkyl or lower alkanoyloxyalkyl, C$_{3-6}$ cycloalkyl, hydroxycycloalkyl, lower alkoxycycloalkyl or lower alkanoyloxycycloalkyl, cycloalkyl lower alkyl, hydroxy-, lower alkoxy- or lower alkanoyloxycycloalkyl lower alkyl, and each of said cycloalkyl moieties is C$_{3-6}$ cycloalkyl; cyano, cyano lower alkyl, lower alkenyl, lower alkynyl, tetrahydrofuryl, mono- or di-lower alkylamino lower alkyl, mono- or di-lower alkylamino lower hydroxy alkyl; unsubstituted or substituted phenyl, unsubstituted or substituted phenyl lower alkyl or unsubstituted or substituted phenyl hydroxy lower alkyl, unsubstituted or substituted diphenyl lower alkyl, unsubstituted or substituted phenyl lower alkenyl, unsubstituted or substituted benzoyl or unsubstituted or substituted benzoyl lower alkyl; unsubstituted thienyl or thienoyl or substituted thienyl or thienoyl, wherein the substituents are one, two or three substituents selected from the group consisting of lower alkyl, lower alkoxy and halogen, $R^4$ is lower alkyl, and Z is hydrogen, lower alkyl or unsubstituted or substituted phenyl, or Z and $R^3$ together with the carbon atom to which they are attached form a $C_{3-6}$ cycloalkyl group, said substituted phenyl and said substituted benzoyl being substituted by one to three substituents selected from lower alkyl, lower alkoxy, halogen or hydroxy, with no more than two hydroxy; whereby the configuration of the substituents at the 3- and 4-position of the depicted piperidine ring is cis, excluding N-($C_{2-6}$ alkyl, $C_{2-6}$ hydroxyalkyl, NN-di-lower alkylamino lower alkyl, or optionally substituted $C_{7-11}$ aralkyl) substituted derivatives of quinicine and cinchonicine.

2. A compound according to claim 1 or a salt thereof, wherein A—B is

—$CH_2$—$CH_2$—, —CHOH—$CH_2$—, —$CH_2$—CHOH—, —$CH_2$—C(O)—, —C($NOR^4$)—$CH_2$— or —$CH_2$—C($NOR^4$)—.

3. A compound according to claim 1, or a salt thereof, wherein $R^3$ is $C_{1-8}$ lower alkoxyalkyl or lower alkanoyloxyalkyl, $C_{3-6}$ cycloalkyl, hydroxycycloalkyl, lower alkoxycycloalkyl or lower alkanoyloxycycloalkyl, cycloalkyl lower alkyl, hydroxy-, lower alkoxy- or lower alkanoyloxycycloalkyl lower alkyl, and each of said cycloalkyl moieties is $C_{3-6}$ cycloalkyl; cyano, cyano lower alkyl, lower alkenyl, lower alkynyl, tetrahydrofuryl, mono- or di-lower alkylamino lower hydroxy-alkyl; unsubstituted or substituted phenylhydroxy lower alkyl, unsubstituted or substituted diphenyl lower alkyl, unsubstituted or substituted phenyl lower alkyl, unsubstituted or substituted phenyl lower alkenyl, unsubstituted or substituted benzoyl or unsubstituted or substituted benzoyl lower alkyl, said substituted phenyl and substituted benzoyl being defined as in claim 1; or $R^3$ is said unsubstituted or substituted thienyl or thienoyl.

4. A compound according to claim 3 or a salt thereof, wherein $R^1$ is hydrogen and A—B is —C(O)—$CH_2$—.

5. A compound according to claim 1 or a salt thereof, wherein $R^1$ is hydrogen or methoxy, A—B is —CHOH—$CH_2$— or —$CH_2$—$CH_2$—, and

is —$(CH_2)_3$—C(O)—Ar, in which Ar is phenyl, thienyl or phenyl substituted by one, two or three fluorine, chlorine or methoxy.

6. A compound according to claim 1 or a salt thereof, wherein $R^1$ is hydrogen or methoxy, A—B is —CHOH—$CH_2$—, —$CH_2$—CHOH— or —$CH_2$—$CH_2$—, Z is hydrogen and $R^3$ is $C_{2-8}$ alkyl, $C_{1-8}$ hydroxyalkyl, or loweralkoxyalkyl.

7. A compound according to claim 1 or a salt thereof, as represented by formula 1e,

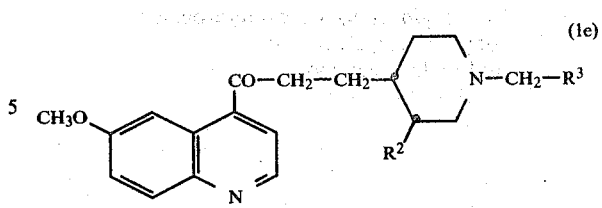

in which $R^2$ is as defined in claim 1, $R^3$ is ethyl, n-butyl, iso-butyl, n-pentyl, iso-pentyl, lower alkoxy lower alkyl, $C_{3-6}$ cycloalkyl lower alkyl, lower alkenyl, unsubstituted or substituted phenyl lower alkyl or unsubstituted or substituted benzoyl or unsubstituted or substituted benzoyl lower alkyl.

8. A compound according to claim 1 or a salt thereof, as represented by formula 1f,

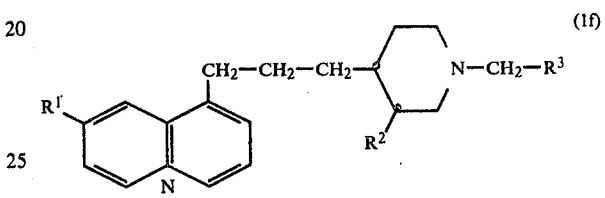

in which $R^1$ and $R^2$ are as defined in claim 1 and $R^3$ is ethyl, n-butyl, iso-butyl, n-pentyl, iso-pentyl, cyclobutyl, lower alkenyl, unsubstituted or substituted phenyl lower alkyl or unsubstituted or substituted benzoyl or unsubstituted or substituted benzoyl lower alkyl.

9. A compound according to claim 1, or a salt thereof, as represented by formula 1g,

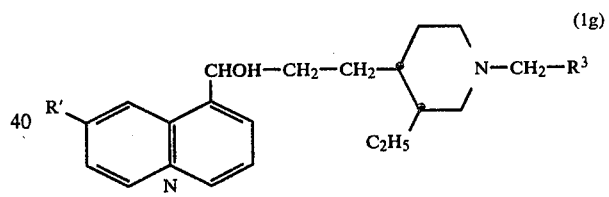

in which $R^1$ is as defined in claim 1 and $R^3$ is $C_{2-8}$ alkyl or —$(CH_2)_n$—C(O)$R^{11}$, wherein $R^{11}$ is said unsubstituted or substituted phenyl and n is 0, 1, 2, 3, or 4.

10. A compound according to claim 1 or a pharmaceutically acceptable salt thereof, as respresented by formula 1i,

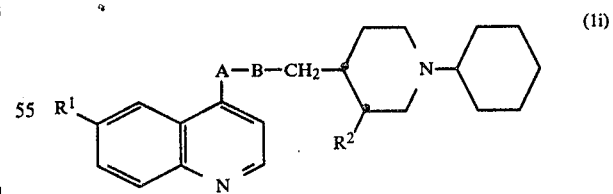

in which A—B, $R^1$ and $R^2$ are as defined in claim 1.

11. A compound according to claim 1, wherein A—B is —$CH_2$—$CH_2$—, —CHOH—$CH_2$— or —C(O)—$CH_2$—.

12. A compound according to claim 7 wherein $R^2$ is vinyl and $R^3$ is 2-benzoylethyl, 2-(4-fluorobenzoyl)ethyl or 1-hydroxy-1-methyl-ethyl.

13. N-(3-benzoylpropyl)-hydrocinchonicine.

14. N-(3-benzoylpropyl)-hydrocinchonicinol-1.

15. N-(3-benzoylpropyl)-desoxo-hydrocinchonicine.
16. N-propyl-hydroquinicinol-1.
17. N-butyl-hydroquinicinol-1.
18. N-pentyl-hydroquinicinol-1.
19. N-pentyl-hydrocinchonicinol-1.
20. N-(4-methoxybutyl)-hydrocinchonicine.

21. A method of treating mammals, including humans, suffering from cardiovascular disease, which comprises administering to the sufferer a therapeutically effective amount of a compound or pharmaceutically acceptable salt thereof according to claim 1.

22. A pharmaceutical composition useful for treating mammals, including humans, suffering from cardiovascular disease, comprising a therapeutically effective amount of a compound or pharmaceutically acceptable salt thereof according to claim 1 in combination with a pharmaceutically acceptable carrier therefor.

* * * * *